United States Patent [19]

Fahim et al.

[11] 4,229,430

[45] Oct. 21, 1980

[54] ORAL COMPOSITION FOR IMPROVING ORAL HEALTH

[76] Inventors: Mostafa S. Fahim, 500 Hulen Dr.; Ercell L. Miller, 3424 Woodrail Ter., both of Columbia, Mo. 65201

[21] Appl. No.: 935,247

[22] Filed: Aug. 21, 1978

[51] Int. Cl.$^3$ ............... A61K 7/16; A61K 31/365; A61K 33/30
[52] U.S. Cl. ...................... 424/49; 424/145; 424/280
[58] Field of Search ............ 424/49, 145, 280

[56] References Cited

U.S. PATENT DOCUMENTS

| | | | |
|---|---|---|---|
| 1,488,097 | 3/1924 | Greger | 424/145 |
| 2,470,906 | 5/1949 | Taylor | 424/55 |
| 3,065,139 | 11/1962 | Ericsson et al. | 424/130 |
| 3,772,431 | 11/1973 | Mlkvy et al. | 424/49 |
| 3,886,265 | 5/1975 | Evers et al. | 424/49 |
| 3,888,976 | 6/1975 | Mlkvy et al. | 424/49 |
| 4,022,880 | 5/1977 | Vinson et al. | 424/49 |

FOREIGN PATENT DOCUMENTS 7102423  8/1972  Netherlands ................ 424/49

*Primary Examiner*—Douglas W. Robinson
*Attorney, Agent, or Firm*—Grace J. Fishel

[57] ABSTRACT

A therapeutic composition is disclosed for use in improving the physiological tone of the oral tissues, which among other beneficial effects nourishes said tissues and causes them to approach normal condition. The therapeutic composition also has an antimicrobial effect on the oral microflora including those difficult to eliminate pathogenic genera known to be implicated in dental caries and periodontal disease. The therapeutic composition comprises a pharmaceutically acceptable, water soluble zinc salt and ascorbic acid or an active analog thereof. The zinc salt and the ascorbic acid are present in an amount sufficient to provide a synergistic combination which has a greater than additive antimicrobial effect on such oral genera as Actinomyces, Streptococcus, Staphylococcus, Candida, Pseudomonas and Escherichia.

10 Claims, No Drawings

ORAL COMPOSITION FOR IMPROVING ORAL HEALTH

This invention relates to a composition for oral administration which improves the physiological tone of the oral tissues and which has an antimicrobial effect on the oral microflora.

All of the causative factors in the etiology of a healthy oral condition are not known. It is known, however, that a reduction in the amount of zinc ions or in the amount of ascorbic acid available to nourish the oral tissues adversely affects their physiological tone. How much of this is the result of enzymatic, microbial and other factors has not been determined. What has been clinically observed, however, is that sometimes the oral tissues become edematous, inflammed and susceptible to microbial attack.

It has been known for centuries that vitamin C deficiency causes scurvy. More recently, it has become known that the formation of normal collagen depends on ascorbic acid. Since ascorbic acid is involved in some hydroxylation reactions, the slowness with which scorbutics commonly heal may be caused by insufficient cross-linking in collagen due to decreased hydroxylation of proline.

It is known that a diet deficient in ascorbic acid or zinc renders the gingiva more susceptible to bacterial attack. Excess amounts of dietary ascorbic acid or zinc, however, do not increase the amount of these materials in the saliva and have no corresponding beneficial effect on the oral tissues.

There have been studies which have shown that the amount of zinc and vitamin C is depleted in the blood and in the cells by stress. It is also known that the plasma concentration of zinc decreases during pregnancy, and among some patients on oral contraceptives. Other studies have shown that zinc plays a role in the taste bud support system and in the mechanism of tastant-receptor binding. Zinc depletion is known to occur in patients taking drugs like Dilantin or in subjects on diets heavy in fiber or phytate. Still other factors are known to interfere with the intestinal absorption or with the utilization of zinc ions as well as of ascorbic acid.

The physiological tone of the oral mucosa, however, is not the only factor in maintaining a healthy oral condition. Epidemiological studies have suggested that microbial plaque is a major factor contributing to dental caries and periodontal disease. Numerous mechanisms by which dental caries may occur have been suggested. According to the most widely accepted concept, specific microbes present in bacterial plaque colonize the surface of the teeth, ferment dietary carbohydrates and produce organic acids. These acids demineralize the teeth, causing the enamel to decay.

Plaque is also implicated in periodontal disease. Although the precise cause of periodontal disease remains unclear, it is widely accepted that the primary cause is bacterial plaque located in the gingival crevice between the surface of the teeth and the gingiva.

Mechanical debridement of plaque by brushing and use of floss is still the primary recommended and accepted method for the prevention of dental caries and periodontal disease. This approach is successful when rigorously practiced but is so highly labor-intensive that most people are not sufficiently motivated to practice it consistently. Since plaque is quickly reformed, continual brushing and flossing are essential to this method of therapy. Moreover, in the presence of gingival inflammation, mechanical methods of plaque removal frequently cause gingival hemorrhage. This often causes the patient to divert from his brushing and flossing regimen.

The focus in oral hygiene has been on a chemical method for dealing with oral plaque. While this clearly would have an obvious clinical advantage for use alone or more effectively in combination with mechanical methods, a more perfect therapeutic composition would also have a beneficial effect on the oral mucosa beyond that of a mere antimicrobial agent.

The problems in just dealing with plaque, however, should not be underestimated. In search of an effective chemical, it is important to keep in mind that the periodontal tissues may be colonized by as many as 150 different species of microorganisms. The particular microbial flora in any given area of the mouth at any given time is the result of the microbial succession that has taken place up to that time. Not all of the oral microflora are implicated in dental caries or in periodontal disease but those pathogenic genera which are responsible are, in general, among those most difficult to kill. Moreover, the net development of dental caries and periodontal disease is the result of the interplay of numerous organisms. From this, it is clear that an effective chemical method of just treating plaque must have a broad antimicrobial spectrum and be effective against those specific organisms that cause the problem.

In search of an effective chemical method for dealing with oral plaque, many chemicals have been tried. Several forms of antibiotics such as penicillin inhibit plaque formation, but the development of resistant organisms and patient sensitivity along with other side effects have seriously restricted their application.

To avoid the problems associated with systemic antibiotics, dental research has focused on antiseptics and on drugs uniquely involved in the biology of the mouth. Among the many materials tested for this purpose have been zinc salts and ascorbic acid. For example, zinc salts have been used as astringents in mouthwashes for the purpose of flocculating and precipitating proteinaceous material so that it can be removed by flushing. Ascorbic acid has been tried in the prevention of dental plaque. U.S. Pat. No. 2,470,906 to R. Taylor.

Combinations of zinc salts with certain other antibacterial agents have been tried. U.S. Pat. No. 4,022,880 to L. Vinson et al. Still others have tried zinc salts with enzymes. U.S. Pat. No. 4,082,841 to M. Pader. Oxidizing preparations containing ascorbic acid, a peroxide and a metal ion catalyst have also been tried. U.S. Pat. No. 3,065,139 to S. Ericsson et al.

It has now been found that a combination of zinc ions and ascorbic acid provides a therapeutic composition which improves the physiological tone of the oral tissues as well as providing a therapeutic composition which is surprisingly effective against the oral microflora responsible for plaque. More particularly, it has been found that when these agents are combined a greater than additive antimicrobial effect can be obtained.

In view of the above, among the several objects of the present invention may be noted the provision of a therapeutic composition for use in improving the physiological tone of the oral tissues and for use in reducing oral plaque. Other objects and features will be in part apparent and in part pointed out hereinafter.

In general, the new compositions embodying the present invention contain a pharmaceutically acceptable, water soluble zinc salt and ascorbic acid or an active analog thereof. To be useful herein for the purpose of both improving physiological tone and reducing plaque, the zinc salt and the ascorbic acid must be present in an amount sufficient to provide a synergistic combination which has a greater than additive antimicrobial effect on the microflora found in the oral cavity. At the heart of the invention is the discovery of such synergistic combinations.

The provision of such a therapeutic composition is a major accomplishment. For example, to be effective for the present purpose, the composition must provide an antiseptic with a broad antimicrobial spectrum. On the other hand, to avoid harming the mucosa, it cannot be too concentrated. Since, as such, it cannot be formulated strong enough to kill all of the organisms right away, it is important that it not be immediately cleared from the oral cavity but continues to be effective for some time thereafter. There is also the diluting effect of the saliva and the reinoculation of the oral cavity to contend with. Since the composition may act by chemical combination with the mucosal and microbial photoplasm, it is important that the therapeutic composition not be inactivated by combination with the constituents of the saliva or exudates of the infections. Finally, it is important that the present combinations be shelf stable and compatible with pharmaceutical carriers and other ingredients normally found in oral preparations. It is a further definite advantage that the combination is relatively inexpensive to formulate.

Insofar as known prior to the present discovery, it was not known that a combination of zinc ions and ascorbic acid could give rise to a synergistic combination if present at effective levels. Nor was it known that such a combination would provide a therapeutic effect after the combination is emptied from the mouth. While some of the benefits observed for higher levels of zinc and ascorbic acid may have been expected, there was no teaching in the prior art as to how those levels could be effectively raised in the oral cavity.

The therapeutic compositions of the present invention comprise a mixture of a pharmaceutically acceptable water soluble zinc salt and ascorbic acid or an active analog thereof. They are non-toxic and innocuous tasting and they produce no normal irritation or allergic reactions. In the context of the present invention, ascorbic acid includes l-ascorbic acid, dehydroascorbic acid and sodium ascorbate. Its active analogs include l-glucoascorbic acid, d-araboascorbic acid, l-rhamnoascorbic acid, 6-desoxy-l-ascorbic acid and the like.

Suitable zinc salts include those zinc compounds which are soluble in water at body temperature. Suitable salts must be pharmaceutically acceptable. As such, they must be safe and organoleptically tolerable in the oral cavity and have no significant side effects either orally or systemically. Among the useful zinc salts are those formed from the following organic and inorganic anions: acetate, benzoate, borate, bromide, carbonate, citrate, chloride, glycerophosphate, hexafluorosilicate, phenolsulfonate, silicate, alkanoates having 6 to 18 carbon atoms, such as zinc stearate, sulfate, tannate, titanate, tetrafluoroborate or the like. If the combination is to be stored, to prevent the oxidation of ascorbic acid, it is preferred that oxidizing zinc salts such as zinc peroxide be avoided. It is also preferred that an antioxidant such as vitamin E be added. The zinc salts may be used singly or in combination but zinc sulfate used alone is preferred.

In accordance with the present invention, the zinc salt and the ascorbic acid is present in that amount sufficient to provide a synergistic combination effective as an antimicrobial agent against such difficult to kill oral microflora as *Actinomyces viscosus,* alpha Streptococcus, *Candida albicans, Escherichia coli, Pseudomonas aeruginosa, Staphylococcus epidermidis* and *Streptococcus mutans.* Excessive amounts of zinc salts beyond that necessary to provide an effective combination should be avoided since such compositions are unpleasantly astringent. Similarly, excessive amounts of ascorbic acid should be avoided since such compositions are unpleasantly acidic. The pH of the mixture is preferably between about 4 and 5, most preferably about 4.5. This can be easily achieved by providing the ascorbic acid partly in the form of sodium ascorbate.

Normally, the zinc salt and ascorbic acid is in a pharmaceutical carrier which may be either a liquid or solid. For example, where the oral composition is a mouthwash, the balance of the preparation may consist of water, ethyl alcohol and a polyhydric alcohol such as glycerol or sorbitol. Flavoring agents and sweeteners may also be added along with stabilizers such as TWEEN 80.

The composition of the present invention can also be formulated as a paste, powder or liquid dentrifrice, chewing gum, tablet, lozenge or the like. When the composition is a toothpaste, there may be present polishing agents, foaming agents and so forth which are compatible with the zinc salt and with the ascorbic acid.

When the zinc salt is $ZnSO_4.7H_2O$, an effective mouthwash is prepared wherein the concentration of said salt is at least 0.5 percent by weight/volume and wherein the ascorbic acid is present in a similar amount. Preferably, the amount of $ZnSO_4.7H_2O$ and the amount of ascorbic acid should not be more than about 2.0 percent by weight/volume to avoid excessive astringency and acidity, respectively. Depending on the solubility of the zinc salt, the amounts thereof must be adjusted to provide an effective synergistic combination.

In use, the therapeutic composition is contacted with the oral tissues for several minutes and then emptied. It has an immediate antimicrobial effect and continues to exert an antimicrobial and therapeutic effect for some time thereafter.

The following examples illustrate the invention.

EXAMPLE 1

A mouthwash was prepared from the following components:
95% Ethyl Alcohol—200 ml
$ZnSO_4.7H_2O$—20 g
Ascorbic Acid—20 g
Glycerin—100 ml
Water q. s.—1000 ml

EXAMPLE 2

Twenty guinea pigs weighing $350 \pm 12$ grams were treated with 4 ml of the mouthwash described in Example 1 twice daily for ninety days. The mouthwash was applied with a sterile cotton swab into the oral cavity of each animal.

The animals were sacrificed after ninety days. Tissues from the gingiva, salivary glands and mucosa of the oral cavity were obtained and fixed for histological examination. The results showed no pathological changes in the tissues and no irritation or edema as compared to ten control animals that received no treatment.

EXAMPLE 3

To evaluate the mouthwash described in Example 1 for its effect in reducing oral plaque and in improving the physiological tone of the oral tissues, sixty patients were clinically observed. The symptoms and conditions presented by the patients were diverse but could be generally divided into five categories: gingivitis periodontitis, periodontal abscess, acute necrotizing ulcerative gingivitis, juvenile periodontitis and desquamative gingivitis.

The patients were asked not to change any of their daily habits or to alter the intake of any medication that they were presently taking. Approximately half of the patients were given the mouthwash described in Example 1. These patients were instructed to use it twice daily, diluting it 1:1 with water, taking a mouthful, holding it in the mouth with agitation for two minutes and then emptying.

The other half of the patients were given a mouthwash like that described in Example 1 but without any ascorbic acid. These patients were also given liquid ascorbic acid and the instruction to put 4 or 5 drops of it in the mouth, hold it for two minutes and then swallow.

Most of the patients were observed at one-week intervals. Before treatment, typical symptoms of unhealthy gingiva were swelling, mild to gross edema and mild to frank hemorrhage. A majority had an obvious disagreeable mouth odor and all had a desire to improve. Consequently, it can be assumed that they were reasonably consistent in the use of the mouthwash and the ascorbic acid as directed.

Those patients with extreme pathological conditions showed marked improvement in 1 to 3 days. In all cases, there was a marked clinical improvement at the end of one week. In most instances, the frank hemorrhage had stopped, edema lessened, appearance of stippling increased and color begun to change from bright red to a lighter pink. At the end of the second and third weeks, the improvement was even more evident.

Without exception, each of the patients said that his mouth and teeth felt cleaner, fresher and more comfortable even after the first day but markedly so after several days' use. All wanted to continue to use the mouthwash. The gingival and periodontal index was determined by the technique described by J. Silliness et al, Acta. Odont. Scand. 22, 121 and by photography before each patient used the mouthwash and 2 weeks, 1 month and 3 months after using the mouthwash. With disclosing wafers, there was obvious clinical evidence of less bacteriological plaque accumulation after using the mouthwash. Plaque accumulation decreased consistently as the patient continued to use the mouthwash.

EXAMPLE 4

To evaluate the mouthwash described in Example 1 for its effect in killing oral bacteria, twenty-three patients ranging in age from 19 to 52 years were tested. The patients were divided into two groups. The patients in Group I were given a placebo mouthwash like that in Example 1 but with no zinc sulfate or ascorbic acid. Those in Group II were given the mouthwash described in Example 1.

Each patient was asked to rinse his mouth with the mouthwash for 2 minutes and then to empty. A swab culture was taken before and at 5, 10 and 30 minute intervals after using the mouthwash. The results are reported in Table I below and show that the mouthwash described in Example 1 significantly decreased the bacteria in the oral cavity even after the mouthwash had been discharged.

TABLE I

| | Number of Bacterial cells/ml | |
|---|---|---|
| | Group I | Group II |
| Before using mouthwash | $4.8 \times 10^7 \pm 0.98$ | $4.9 \times 10^7 + 0.78$ |
| 5 minutes after mouthwash | $4.7 \times 10^7\ 0.65$ | $3.1 \times 10^6 \pm 0.45$ |
| 10 minutes after mouthwash | $4.9 \times 10^7 \pm 0.74$ | $1.3 \times 10^6\ 0.61$ |
| 30 minutes after mouthwash | $4.8 \times 10^7 \pm 0.34$ | $0.5 \times 10^6\ 0.04$ |

EXAMPLE 5

Seventeen pregnant women, ranging in age from 20 to 32 years, in the third trimester, suffering from pregnancy gingivitis were examined and classified into one of two categories. Those with gingivitis without any hyperplastic signs and those with gingivitis gravidarum. Seven of the patients were classified as having gingivitis without any hyperplastic signs and ten patients were classified as having gingivitis gravidarum with hyperplastic signs.

Patients were divided into two groups for treatment. Three patients from the first category and five patients from the second category were given daily amounts of 50 mg of $ZnSO_4.7H_2O$ and 100 mg of vitamin C orally for one month.

The remaining nine patients were given the mouthwash described in Example 1 and instructed to use it twice daily.

The treatment with orally administered zinc sulfate and ascorbic acid was not effective. There was no increase in the zinc or ascorbic acid levels in the saliva but there was an increase in the blood level due to the treatment.

With the other patients, bleeding stopped after one week and the gingiva returned to its normal pink color after one month. Ascorbic acid in the saliva increased from 15.6 $\mu$g/gram to 31.2 $\mu$g/gram and the zinc level in the saliva increased from 10 $\mu$g/gram to 18.6 $\mu$g/gram. Hence, it is seen that treatment with the mouthwash of Example 1 during pregnancy has a greater effect than treatment with zinc salt and vitamin C orally.

EXAMPLE 6

Eleven patients suffering with canker sores, not of herpes simplex origin, were instructed to rinse three times a day with the mouthwash described in Example 1. After one day, the patients were relieved and could drink acidic liquids such as orange juice which had been painful before. After four days, the canker sores were completely healed and the treatment was stopped.

In the first year, the patients had recurrent canker sores six times. Each time, the sores were treated for four days. In the second year, they experienced recurrence two times, in the third year there was no recurrence. The patients have been followed four years. To date there has been no recurrence.

Eight other patients with canker sores, not of herpes simplex origin, were instructed to use the mouthwash described in Example 1 twice a day, once in the morning and once before bedtime. In the first year, the patients experienced recurrent sores three to four times a year. In the second year, there has been no recurrence.

EXAMPLE 7

Sixteen men suffering with throat infection were given the mouthwash described in Example 1 and advised to use it twice a day for a week. Before treatment, swab cultures revealed heavy growth of alpha Streptococcus, *Staphylococcus epidermidis, Escherichia coli* and *Candida albicans.*

At the beginning of the treatment, some of the patients could not swallow food due to the infection. Twenty-four hours after using the mouthwash, the situation had eased. All patients could eat normally after two days. After six days, swab cultures revealed no growth of the above-mentioned organisms. No adverse side effects or discomfort because of the treatment was noted.

EXAMPLE 8

A mouthwash was prepared from the following components:
95% Ethyl alcohol—200 ml
$ZnSO_4.7H_2O$—20 g
Ascorbic acid—20 g
TWEEN 80*—100 ml
Vitamin E—1,000 I. U.
Water, q.s.—1,000 ml
*polyoxyethylene sorbitan monooleate

EXAMPLE 9

Sixty-three patients ranging in age from 40 to 68 years were tested for taste acuity determined by measurement of the detection and recognition thresholds for four taste qualities: NaCl for salt, sucrose for sweet, HCl for sour and urea for bitter. Twenty-two of the patients had normal taste and 41 had idiopathic hypogeusia.

Each of the hypogeusia patients was instructed to rinse his mouth twice a day with the mouthwash provided therefor. To note the placebo effect, nine of the idiopathic hypogeusia patients were given a placebo like the mouthwash described in Example 8 but without zinc sulfate or ascorbic acid. All of the other patients used the mouthwash described in Example 8. Parotid saliva was collected before treatment and one and three months after treatment. The results are reported in Table II below. The hypogeusia patients receiving the placebo did not improve during the 3 month trial period but the taste of the patients using the mouthwash described in Example 8 improved after one month and became normal after three months.

TABLE II

| | | Zinc Concentration ppb in Salvia | | |
|---|---|---|---|---|
| | Mouthwash | Before | One Month | Three Months |
| Normal | Placebo | 49 ± 16 | 53 ± 12 | 50 ± 18 |
| Hypogeusia | Example 18 | 13 ± 2 | 38 ± 10 | 47 ± 13 |

EXAMPLE 10

In this example, zinc sulfate and ascorbic acid was checked for its effectiveness on two of the bacterial species known to be implicated in dental plaque. These results were then compared with the effect of a synergistic combination of zinc sulfate and ascorbic acid.

Culture media were prepared with $ZnSO_4.7H_2O$ or ascorbic acid or a combination thereof in Tryplic Soy Broth and in a concentration of 0.5, 1, 2, 4, 8 or 10 percent by weight/volume. These broths were then placed in 1 ml tubes and 0.001 ml of an inoculum containing $1 \times 10^8$ alpha Streptococci cells/ml or the same concentration of *Staphylococcus epidermidis* was added to the tubes. The tubes were then incubated over night and the bacterial growth was determined the next day.

All of the tubes showed no growth in the streptococci-inoculated media in the presence of all levels of zinc sulfate or ascorbic acid. In the case of the staphylococci-inoculated media, 80 percent of the cultured bacteria were killed in the presence of 0.5 percent by weight/volume of $ZnSO_4.7H_2O$ or ascorbic acid.

When the concentration of the $ZnSO_4.7H_2O$ or ascorbic acid was increased to 5 percent by weight/volume, all of the staphylococci were also killed. The same result, however, was obtained with a combination of 0.5 percent $ZnSO_4.7H_2O$ with 0.5 percent ascorbic acid. This indicates a synergistic effect between zinc ions and ascorbic acid in their antimicrobial activity against the organisms tested.

EXAMPLE 11

In this example the effect of the mouthwash prepared in Example 1 was tested against the same bacteria as in Example 10. An 0.001 ml aliquant of a staphylococcus inoculum containing $6 \times 10^{11}$ cells/ml or a similar aliquant of a streptococcus inoculum containing $4.2 \times 10^{10}$ cells/ml was added to a test tube.

A volume of the mouthwash described in Example 1 was added to each tube such that the concentration of $ZnSO_4.7H_2O$ and ascorbic acid were both 0.5 percent by weight/volume. In another set of experiments, the mouthwash of Example 1 was diluted with water 1:1 such that the concentration of the zinc sulfate and acid was half of that described above.

The concentration of the bacteria was then determined after 30 sec and after 1, 2, 5 and 30 minutes. The results are reported in Table III below.

TABLE III

| | 30 sec | 1 min | 2 min | 5 min | 30 min |
|---|---|---|---|---|---|
| Mouthwash from Example 1 Concentrated | | | | | |
| Staphylococcus | NG* | NG | NG | NG | NG |
| Streptococcus | $3 \times 10^6$ | NG | NG | NG | NG |
| Diluted 1:1 | | | | | |
| Staphylococcus | $3 \times 10^5$ | $4 \times 10^5$ | $9 \times 10^4$ | $6 \times 10^4$ | $1 \times 10^3$ |
| Streptococcus | $1.5 \times 10^6$ | $2.9 \times 10^6$ | $2.3 \times 10^5$ | NG | NG |

*No Growth

EXAMPLE 12

Culture media were prepared with $ZnSO_4.7H_2O$ or ascorbic acid or a combination thereof in Tryplic Soy Broth as described in Example 10. These broths were then inoculated with 0.1 ml of an inoculum containing $8 \times 10^8$ cells/ml of *Escherichia coli* ATCC-25922 or $5 \times 10^8$ cells/ml of *Pseudomonas aeruginosa.* The results are reported in Table IV below wherein and throughout the following examples the symbol H+ indicates that there was heavy growth, M+ moderate growth, S+ scant growth and NG that there was no growth.

TABLE IV

| | \multicolumn{7}{c}{Concentration percent by weight/volume} |
|---|---|---|---|---|---|---|---|
| | 0.25 | 0.5 | 1.0 | 2.0 | 4.0 | 8.0 | Control |
| $ZnSO_4 \cdot 7H_2O$ | | | | | | | |
| E. coli | — | H+ | NG | NG | NG | NG | H+ |
| P. aeruginosa | — | H+ | S+ | S+ | S+ | S+ | H+ |
| Ascorbic acid | | | | | | | |
| E. coli | — | S+ | H+ | NG | NG | NG | H+ |
| P. aeruginosa | — | H+ | M+ | S+ | NG | NG | H+ |
| Combination $ZnSO_4 \cdot 7H_2O$ and ascorbic acid | | | | | | | |
| E. coli | H+ | M+ | S+ | NG | NG | — | H+ |
| P. aeruginosa | S+ | S+ | NG | NG | NG | — | H+ |

EXAMPLE 13

The effectiveness of the mouthwash described in Example 1 was tested for its antimicrobial effect on *Streptococcus mutans*, ATCC No. 25175, *Actinomyces viscosus*, ATCC No. 19246 and *Candida albicans*, ATCC No. 18804. It was found effective in inhibiting the growth of all of the test organisms.

EXAMPLE 14

The effectiveness of zinc salts, ascorbic acid and a combination thereof was tried in an amount below that necessary for a synergistic combination. More particularly, $ZnSO_4 \cdot 7H_2O$, ascorbic acid and combinations thereof were tested at the 0.1, 0.2, 0.3 and 0.4 percent by weight/volume level for its antimicrobial effect against alpha Streptococcus, *Streptococcus mutans*, *Staphylococcus aureus*, *Staphylococcus epidermidis*, *Actinomyces israeli* and *Actinomyces viscosus*. All samples showed heavy growth with zinc alone, ascorbic acid alone or their 1:1 combination at the 0.1, 0.2, 0.3 and 0.4 concentrations.

EXAMPLE 15

The effectiveness of the mouthwash described in Example 1 in the presence of biological fluids such as sterile animal serum was tested for its antimicrobial effect on alpha Streptococci and *Staphylococcus epidermidis*. It was found that the mouthwash was effective against these organisms in the presence of the serum.

EXAMPLE 16

Ascorbic acid when dissolved in water tends to oxidize and is not stable for a long period of time. However, when $ZnSO_4 \cdot 7H_2O$ is added to an ascorbic acid solution, it becomes more stable. Stability can be extended to one year by adding 1000 I. U. Vitamin E per liter of solution containing 0.5 percent by weight/volume of $ZnSO_4 \cdot 7H_2O$ and of ascorbic acid. The results of these tests are reported in Table V below.

TABLE V

| | \multicolumn{5}{c}{Active Ascorbic Acid} |
|---|---|---|---|---|---|
| | 0 | 1 month | 3 months | 6 months | 1 year |
| 2% Ascorbic acid | 20 | 16.6 | 15.4 | 12.2 | 10.1 |
| 2% Ascorbic acid and $ZnSO_4 \cdot 7H_2O$ | 20 | 20 | 19.8 | 18.7 | 17.6 |
| Mouthwash Example 1 | 20 | 20 | 20 | 19.6 | 18.4 |
| Mouthwash Example 18 | 20 | 20 | 20 | 20 | 19.5 |

From the above, it is seen that TWEEN also increases the stability of the vitamin C.

In view of the above, it will be seen that the several objects of the invention are achieved and other advantageous results attained. As various changes could be made in the above compositions and methods without departing from the scope of the invention, it is intended that all matter contained in the above description shall be interpreted as illustrative and not in a limiting sense. The invention accordingly comprises the compositions and methods hereinbefore described, the scope of the invention being indicated by the subjoined claims.

What is claimed is:

1. A therapeutic composition for topical oral administration for stimulating production of collagen consisting essentially of about 0.5 to about 2.0 percent by weight/volume of a pharmaceutically acceptable, water soluble zinc salt and about 0.5 to about 2.0 percent by weight/volume of ascorbic acid or sodium ascorbate.

2. The composition according to claim 1 wherein the ratio of the zinc salt to the ascorbic acid or sodium ascorbate is substantially 1 to 1 by weight.

3. The composition according ing to claim 2 wherein the zinc salt is $ZnSO_4 \cdot 7H_2O$.

4. The composition according to claim 3 wherein the pH is from about 4 to about 5.

5. A method for treating oral tissues by stimulating the production of collagen comprising topically administering thereto a therapeutically effective amount of a composition consisting essentially of about 0.5 to about 2.0 percent by weight/volume of a pharmaceutically acceptable, water soluble zinc salt and about 0.5 to about 2.0 percent by weight/volume of ascorbic acid or sodium ascorbate.

6. The method according to claim 5 wherein the composition has a pH from about 4 to about 5 and includes $ZnSO_4 \cdot 7H_2O$ and sodium ascorbate.

7. The method according to claim 6 wherein the ratio of the $ZnSO_4 \cdot 7H_2O$ to the sodium ascorbate is substantially 1 to 1 by weight.

8. A method for treating pregnancy gingivitis comprising topically administering to oral tissues a therapeutically effective amount of a composition consisting essentially of about 0.5 to about 2.0 percent by weight/volume of a pharmaceutically acceptable, water soluble zinc salt and about 0.5 to about 2.0 percent by weight/volume of ascorbic acid or sodium ascorbate.

9. A method for treating oral canker sores comprising topically administering to oral tissues a therapeutically effective amount of a composition consisting essentially of about 0.5 to about 2.0 percent by weight/volume of a pharmaceutically acceptable, water soluble zinc salt and about 0.5 to about 2.0 percent by weight/volume of ascorbic acid or sodium ascorbate.

10. A method for treating idopathic hypogeusia comprising topically administering to oral tissues a therapeutically effective amount of a composition consisting essentially of about 0.5 to about 2.0 percent by weight/volume of a pharmaceutically acceptable, water soluble zinc salt and about 0.5 to about 2.0 percent by weight/volume of ascorbic acid or sodium ascorbate.

* * * * *

UNITED STATES PATENT AND TRADEMARK OFFICE
CERTIFICATE OF CORRECTION

PATENT NO. : 4,229,430

DATED : October 21, 1980

INVENTOR(S) : Mostafa S. Fahim and Ercell L. Miller

It is certified that error appears in the above-identified patent and that said Letters Patent are hereby corrected as shown below:

Column 3, line 24, "photo-" should read "proto-"; line 54, "zine" should read "zinc". Column 6, Table I, there should be a + after each superscript to the base 10. Column 8, Table III, under "1 min", Streptococcus should read "$2.9 \times 10^5$".

Signed and Sealed this

Fifth Day of May 1981

[SEAL]

Attest:

RENE D. TEGTMEYER

Attesting Officer   Acting Commissioner of Patents and Trademarks